(12) United States Patent
Song et al.

(10) Patent No.: US 12,150,944 B2
(45) Date of Patent: Nov. 26, 2024

(54) USE OF ANTI-HER2 ANTIBODY-DRUG CONJUGATE IN CANCER TREATMENT

(71) Applicant: SICHUAN KELUN-BIOTECH BIOPHARMACEUTICAL CO., LTD., Sichuan (CN)

(72) Inventors: Hongmei Song, Sichuan (CN); Xiaoxi Yuan, Sichuan (CN); Jing Wang, Sichuan (CN); Liang Xiao, Sichuan (CN); Tongtong Xue, Sichuan (CN); Ping Liu, Sichuan (CN); Lichun Wang, Sichuan (CN); Jingyi Wang, Sichuan (CN)

(73) Assignee: SICHUAN KELUN-BIOTECH BIOPHARMACEUTICAL CO., LTD., Sichuan (CN)

( * ) Notice: Subject to any disclaimer, the term of this patent is extended or adjusted under 35 U.S.C. 154(b) by 1114 days.

(21) Appl. No.: 16/979,251

(22) PCT Filed: Apr. 30, 2019

(86) PCT No.: PCT/CN2019/085077
§ 371 (c)(1),
(2) Date: Sep. 9, 2020

(87) PCT Pub. No.: WO2019/214492
PCT Pub. Date: Nov. 14, 2019

(65) Prior Publication Data
US 2021/0000970 A1 Jan. 7, 2021

(30) Foreign Application Priority Data
May 11, 2018 (CN) .......................... 201810450156.8

(51) Int. Cl.
A61K 47/68 (2017.01)
A61K 9/00 (2006.01)
A61K 31/337 (2006.01)
A61K 31/555 (2006.01)
A61P 35/00 (2006.01)
C07K 16/32 (2006.01)

(52) U.S. Cl.
CPC .......... *A61K 31/555* (2013.01); *A61K 9/0019* (2013.01); *A61K 31/337* (2013.01); *A61K 47/68031* (2023.08); *A61K 47/6851* (2017.08); *A61P 35/00* (2018.01); *C07K 16/32* (2013.01)

(58) Field of Classification Search
CPC .............. A61K 47/6851; A61K 9/0019; A61K 31/337; A61K 31/555; A61K 47/6803; A61K 47/68031; A61K 2039/505; A61K 47/6855; A61K 31/536; A61P 35/00; C07K 16/32
See application file for complete search history.

(56) References Cited

FOREIGN PATENT DOCUMENTS

| CN | 103288957 A | 9/2013 | | |
|---|---|---|---|---|
| CN | 106470708 A | 3/2017 | | |
| WO | 2015/162293 A1 | 10/2015 | | |
| WO | WO-2016123412 A1 | * 8/2016 | ......... | A61K 47/6811 |
| WO | 2017088734 A1 | 1/2017 | | |

OTHER PUBLICATIONS

Hervent A-S et al. Molecular Mechanisms of Cardiotoxicity Induced by ErbB Receptor Inhibitor Cancer Therapeutics Int. J. Mol. Sci. 2012, 13, 12268-12286; doi:10.3390/ijms131012268 (Year: 2012).*
Abrahao-Machado LF et al. HER2 testing in gastric cancer: An update. (World J Gastroenterol. May 21, 2016; 22(19): 4619-4625 (Year: 2016).*
Lichtman MA et al. A Bacterial Cause of Cancer: An Historical Essay. The Oncologist2017; 22(5); 542-548 (Year: 2017).*
Hanahan D et al. Hallmarks of Cancer: The Next Generation. Cell 2011 144(5) p. 646-674 (Year: 2011).*
Lee KW et al. Molecular targets of phytochemicals for cancer prevention. Nature Reviews Cancer 2011 11 211-218 (Year: 2011).*
Zhang Z et al. Drug metabolism in drug discovery and development. Acta Pharm Sin B. Sep. 2018; 8(5): 721-732 (Year: 2018).*
Almagro JC & Fransson J, Humanization of antibodies. Frontiers in Bioscience 2008; 13:1619-33 (Year: 2008).*
Doi T et al. Safety, pharmacokinetics, and antitumor activity of trastuzumab deruxtecan (DS-8201), a HER2-targeting antibody-drug conjugate, in patients with advanced breast and gastric or gastro-esophageal tumors: a phase 1 dose-escalation study (Lancet Oncol 2017; 18: 1512-22) (Year: 2017).*
Xu J et al. HER2 overexpression reverses the relative resistance of EGFR-mutant H1975 cell line to gefitinib. (Oncol Lett. Dec. 2016 ; 12(6): 5363-5369). (Year: 2016).*
International Search Report for PCT/CN2019/085077 dated Aug. 7, 2019, 4 pages.
The First Office Action mailed Jul. 7, 2023 in corresponding Chinese Patent Application No. 201980018635.5 (with English machine translation)(13 pages).
The Second Office Action mailed May 24, 2024 in corresponding Chinese Patent Application No. 201980018635.5 (with English machine translation)(13 pages).
Wang et al., "Development and Properties of Valine-Alanine based Antibody-Drug Conjugates with Monomethyl Auristatin E as the Potent Payload", International Journal of Molecular Sciences, Aug. 25, 2017 (19 pages).

* cited by examiner

Primary Examiner — Karen A. Canella
Assistant Examiner — John J Skoko, III
(74) Attorney, Agent, or Firm — Rothwell, Figg, Ernst & Manbeck, P.C.

(57) ABSTRACT

Disclosed in the present invention is the use of an anti-HER2 antibody-drug conjugate in cancer treatment. Further provided in the present invention is the use of a pharmaceutically acceptable salt, stereoisomer, or metabolite thereof, or a solvate of each of the foregoing in the manufacture of a medicament for the prophylaxis and/or treatment of a cancer insensitive or irresponsive to a treatment with a HER2-targeting agent.

26 Claims, 2 Drawing Sheets

USE OF ANTI-HER2 ANTIBODY-DRUG CONJUGATE IN CANCER TREATMENT

CROSS REFERENCE TO RELATED APPLICATION

This application is a 35 U.S.C. § 371 National Phase Entry Application from PCT/CN2019/085077, filed Apr. 30, 2019, which claims priority to Chinese Patent Application No. 201810450156.8, filed May 11, 2018, priority is claimed to each of the foregoing and the disclosures of which are incorporated herein in their entirety by reference.

FIELD OF THE INVENTION

The present invention pertains to the field of biomedical technology. In particular, the present invention relates to use of an anti-HER2 antibody-drug conjugate in cancer treatment.

BACKGROUND OF THE INVENTION

Antibody-drug conjugates (ADCs), as novel medicines for targeted therapy, usher in a new era of cancer therapy. With Seattle Genetics, Inc. and ImmunoGen, Inc in the lead, many multinational pharmaceutical enterprises and start-ups are involved in the research and development in this field. According to a report from Market Research, there are currently a total of 45 ADCs in clinical trials worldwide.

An ADC can transport a drug conjugated to an antibody to target cells precisely by the targeting capability of the antibody, thereby effectively increasing local drug concentration at the disease site while greatly lowering drug concentration in other tissues or organs to achieve increased efficacy and reduced toxicity. The polyclonal and monoclonal antibodies used in these strategies have been reported (Rowland et al., 1986, Cancer Immunol. Immunother., 21: 183-87). The antibodies in the ADCs clinically used at present are mostly humanized antibodies, e.g., those in PSMA ADC (anti-PSMA antibody-MMAE conjugate), SGN-75 (anti-CD70 antibody-MMAF conjugate) and T-DM1 (Trastuzumab-DM1 conjugate) are all humanized antibodies. So far, FDA-approved ADCs include Kadcyla® (T-DM1), Mylotarg® (Gemtuzumab ozogamicin), Besponsa® (inotuzumab ozogamicin) and SGN-35.

The anti-HER2 antibody drug, Trastuzumab, has been used clinically for the treatment of HER2-overexpressing breast cancer. In a clinical trial, 15% of the breast cancer patients with immunohistochemistry (IHC) levels above 2+ had a clinical response to Trastuzumab, and the median duration of response was 9.1 months (see e.g., Cobleigh et al., 1996, Journal of Clinical Oncology, 14: 737-744). Trastuzumab (Herceptin) was approved by the US Food and Drug Administration (FDA) on Sep. 25, 1998 for the treatment of patients suffering from HER2-overexpressing breast cancer.

Although Trastuzumab, which is currently a first-line agent of choice for HER2-positive breast cancer, has saved some breast cancer patients or prolonged patients' survival, it is only effective in HER2-overexpressing patients, which constitute about 15% of breast cancer patients in clinics, while did not show a therapeutic effect in many patients with low HER2 expression. It has been found in clinical studies that many patients suffering from HER2-positive breast cancer are insensitive to Trastuzumab as well.

In addition, in therapies with Trastuzumab, many drug-sensitive patients gradually became drug-resistant. There may be various mechanisms in the development of drug resistance, such as structural changes of HER2 receptor molecules, changes of the PI3K/AKT signaling pathway, or the involvement of an immune mechanism. In the case where drug resistance to Trastuzumab develops, the typical choice of medication regimen in domestic clinical practice is lapatinib+xeloda (capecitabine).

The ADC drug Kadcyla® (T-DM1), constructed based on Trastuzumab and the cytotoxic agent DM1, was approved for HER2-positive metastatic breast cancer for which a therapy with taxane and Trastuzumab was previously conducted. T-DM1 is recommended in the guidelines from NCCN (National Comprehensive Cancer Network) as a second-line therapeutic regimen of choice after failure of a treatment with Trastuzumab. Although T-DM1 has achieved impressive clinical efficacy in many patients, the intrinsic drug resistance and acquired drug resistance to it have become a challenge (Ríos-Luci C et al., Cancer Res., Sep. 1, 2017, 77 (17): 4639-4651). Although HER2-positive metastatic breast cancer seems to have relatively low intrinsic drug resistance to T-DM1, most patients treated with T-DM1 would develop acquired drug resistance (Barok M et al., Breast Cancer Res., Mar. 5, 2014, 16(2): 209), suggesting that acquired drug resistance to T-DM1 is a common issue.

WO 2017088734 provides an anti-HER2 antibody-drug conjugate, which was found in a comparative study with T-DM1 to have better therapeutic activity on HER2-positive tumors than T-DM1. However, this document does not include a study on the method and effect of treatment of a cancer insensitive or irresponsive to a treatment with a HER2-targeting agent such as Trastuzumab or T-DM1 (e.g., HER2-positive cancer with drug resistance or cancer with low HER2 expression).

SUMMARY OF THE INVENTION

In a first aspect, the present invention provides use of a conjugate of Formula (I), a pharmaceutically acceptable salt, stereoisomer or metabolite thereof, or a solvate of the foregoing in the manufacture of a medicament for the prophylaxis and/or treatment of a cancer insensitive or irresponsive to a treatment with a HER2-targeting agent,

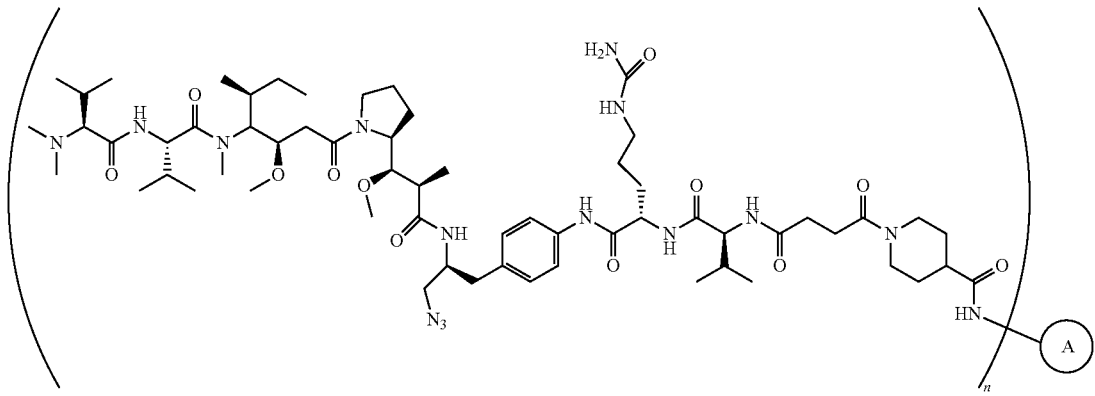

Formula (I)

wherein

A is a moiety obtained after the removal of n amino groups from an anti-HER2 antibody or an active fragment or variant thereof, preferably, A is a moiety obtained after the removal of n amino groups from Trastuzumab or Pertuzumab, and n is an integer of 1, 2, 3, 4, 5, 6, 7, or 8.

In a second aspect, the present invention provides a conjugate of Formula (I), a pharmaceutically acceptable salt, stereoisomer or metabolite thereof, or a solvate of the foregoing, as described above, for use in the prophylaxis and/or treatment of a cancer insensitive or irresponsive to a treatment with a HER2-targeting agent.

In a third aspect, the present invention provides a method of preventing and/or treating a cancer insensitive or irresponsive to a treatment with a HER2-targeting agent, comprising administering a therapeutically effective amount of a conjugate of Formula (I), a pharmaceutically acceptable salt, stereoisomer or metabolite thereof, or a solvate of the foregoing, as described above, to a subject in need thereof.

DETAILED DESCRIPTION OF THE INVENTION

Definitions

Figure 1:
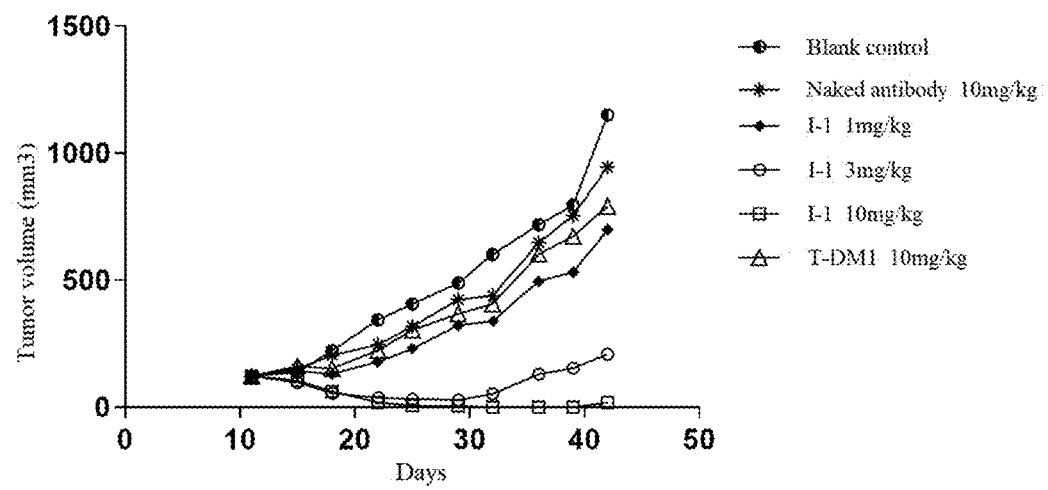
FIG. 1 shows the changes in tumor growth by volume of the mice in each group in a human breast cancer JIMT-1 model.

Unless otherwise defined, all the terms used herein have the same meaning as commonly understood by one of ordinary skill in the art. Relevant definitions and terms can be found in e.g., Current Protocols in Molecular Biology (Ausubel).

All references mentioned throughout the specification are incorporated herein by reference in their entirety.

The term "HER2" refers to the native sequence of human HER2 protein (Genbank accession number X03363, see e.g., Semba et al., (1985) PNAS, 82: 6497-6501; and Yamamoto et al., (1986) Nature, 319: 230-234), and functional derivatives thereof, e.g., amino acid sequence variants.

The native sequence of Her2 as used herein can be isolated from nature, or can be produced by recombinant DNA technology, chemical synthesis, or a combination thereof.

The term "antibody" as used herein is used in the broadest sense and covers complete monoclonal antibodies, polyclonal antibodies, and multispecific antibodies formed from at least two complete antibodies (e.g., bispecific antibodies), so long as they exhibit the desired biological activity.

The term "monoclonal antibody" as used herein refers to an antibody obtained from a population of substantially homogeneous antibodies, i.e., the individual antibodies constituting the population are identical except for possible naturally occurring mutations that may be present in minor amounts. Monoclonal antibodies are highly specific to a single antigenic determinant (epitope), and in contrast, polyclonal antibodies include different antibodies directed against different determinants (epitopes). Besides specificity, monoclonal antibodies are advantageous in that they can be synthesized without contamination by other antibodies. Here the modifier "monoclonal" indicates the character of the antibody as being obtained from a substantially homogeneous population of antibodies, but should not be construed as requiring any particular production method.

The monoclonal antibodies as used herein specifically include chimeric antibodies in which a portion of the heavy and/or light chain is identical or homologous to corresponding sequences in antibodies of a certain species, a certain class, or a certain subclass, while the remainder of the chain(s) is identical or homologous to corresponding sequences in antibodies of another species, another class, or another subclass, so long as they exhibit the desired biological activity (see e.g. U.S. Pat. No. 4,816,567; and Morrison et al., (1984) Proc. Natl. Acad. Sci. USA, 81: 6851-6855). Chimeric antibodies that can be used in the present invention include primatized antibodies comprising variable domain antigen-binding sequences from a non-human primate (e.g., old world monkey, gorilla, etc.) and human constant region sequences.

The term "antibody fragment" refers to a portion of an antibody, preferably the antigen-binding or variable region thereof. Examples of antibody fragment include Fab, Fab', F(ab')$_2$, and Fv fragments; diabodies; linear antibodies; and single-chain antibody molecules.

The term "bispecific antibody" is also known as "bifunctional antibody conjugate", and refers to a conjugate formed by a first antibody (fragment) and a second antibody (fragment) through a coupling arm, and the activity of the respective antibodies is remained in the conjugate, which thus has a dual function and dual specificity.

The term "multispecific antibody" includes, for example, tri- and tetra-specific antibodies, the former is an antibody having three different types of antigen-binding specificity, and the latter is one having four different types of antigen-binding specificity.

The term "intact antibody" refers to an antibody comprising an antigen-binding variable region, as well as a light chain constant domain (CL) and heavy chain constant domains (CHL CH2 and CH3). The constant domains may be native sequences (e.g., human native sequence constant domains) or amino acid sequence variants thereof. An intact antibody having one or more effector functions is preferred.

"Humanized" forms of non-human (e.g., mouse) antibodies refer to chimeric antibodies that contain minimal sequence derived from non-human immunoglobulin. Most humanized antibodies are immunoglobulins of a human recipient in which residues from a hypervariable region are replaced by residues from a hypervariable region of a non-human (e.g., mouse, rat, rabbit or nonhuman primate) species (donor antibody) having the desired specificity, affinity, and capacity. In some embodiments, framework region (FR) residues of the human immunoglobulin are also replaced by non-human residues. Furthermore, humanized antibodies may comprise residues that are not found in the recipient antibody or in the donor antibody. These modifications are made to further optimize antibody performance. A humanized antibody generally comprises at least one, and typically two variable domains, in which all or substantially all of the hypervariable loops correspond to those of a non-human immunoglobulin, and all or substantially all of the FRs are those of a human immunoglobulin sequence. The humanized antibody can also comprise at least a portion of an immunoglobulin constant region (Fc, typically Fc of a human immunoglobulin). For details, see e.g., Jones et al., 1986, Nature, 321: 522-525; Riechmann et al., 1988, Nature, 332: 323-329; and Presta, 1992, Curr. Op. Struct. Bwl 2: 593-596.

Depending on the amino acid sequence of the constant domain of their heavy chains, intact antibodies can be assigned to different "classes". The five major classes are IgA, IgD, IgE, IgG, and IgM, and several of these may be further divided into "subclasses" (isotypes), e.g., IgG1, IgG2, IgG3, IgG4, IgA1, and IgA2. The heavy-chain constant domains of different classes of antibodies are known as α, δ, ε, γ, and μ, respectively. The subunit structures and three-dimensional configurations of different classes of immunoglobulins are well known in the art.

In the present specification, although amino acid substitutions in antibodies are substitutions with L-amino acids in most cases, they are not limited thereto. In some embodiments, the peptide chains of an antibody may comprise one or more D-amino acids. Peptides containing D-amino acids are thought to be more stable and less prone to degradation in oral cavity, gut or plasma than peptides composed exclusively of L-amino acids.

Monoclonal antibodies used in the present invention can be produced by various methods. For example, monoclonal antibodies for use in the present invention can be obtained by a hybridoma method using various species (including cells of mice, hamsters, rats and human) (see e.g., Kohler et al., 1975, Nature, 256: 495), or by a recombinant DNA technology (see e.g., U.S. Pat. No. 4,816,567), or by isolation from phage antibody libraries (see e.g., Clackson et al., 1991, Nature, 352: 624-628; and Marks et al., 1991, Journal of Molecular Biology, 222: 581-597).

The anti-HER2 antibody in the present invention is preferably an anti-human HER2 antibody. Preferably, the CDR1, CDR2 and/or CDR3 in the heavy and light chains of the anti-human HER2 antibody are the CDR1, CDR2 and/or CDR3 in the heavy and light chains of Trastuzumab, respectively. The anti-human HER2 antibody can be a humanized antibody or a fully human antibody.

More preferably, the anti-HER2 antibody used in the present invention is a humanized mouse anti-human Her2 antibody 4D5 shown in FIG. 1 of U.S. Pat. No. 5,821,337.

Particularly preferably, the antibody used in the present invention is Trastuzumab, the sequence of which has been disclosed in e.g., CN 103319599A. The Lys at the end of the heavy chain of Trastuzumab is apt to delete, which, however, does not affect biological activity, see Dick, L. W. et al., Biotechnol. Bioeng., 100: 1132-1143. Trastuzumab, the sequence thereof wherein the Lys at the end of the heavy chain is deleted, or fragment thereof, as mentioned above, are all within the scope of Trastuzumab of the present invention.

The term "cytotoxic agent" as used herein refers to a substance that inhibits or prevents the function of cells and/or causes destruction of cells.

The antibody-drug conjugate of the present invention can be in the form of a pharmaceutically acceptable salt, or stereoisomer, or metabolites, or solvate, and the salt, stereoisomer, or metabolite can also be in the form of a solvate.

The term "pharmaceutically acceptable salt" refers to a salt that keeps the biological availability and nature of a compound, and meets the requirements for a medicine in terms of biological or other aspects. In many cases, the antibody-drug conjugate of the present invention forms an acid addition salt and/or base addition salt via an amino group and/or a carboxyl group or other similar groups therein.

Pharmaceutically acceptable acid addition salts can be those formed with inorganic acids or organic acids. The inorganic acids include, e.g., hydrochloric acid, hydrobromic acid, sulfuric acid, nitric acid, and phosphorus acid, etc. The organic acids include, e.g., acetic acid, propionic acid, hydroxyacetic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid, etc.

Pharmaceutically acceptable base addition salts can be those formed with inorganic bases or organic bases. The salts formed with inorganic bases include, e.g., sodium salts, potassium salts, lithium salts, ammonium salts, calcium salts, magnesium salts, iron salts, zinc salts, copper salts, manganese salts, and aluminium salts, etc., and ammonium salts, potassium salts, sodium salts, calcium salts, and magnesium salts are particularly preferred. The organic bases include, e.g., primary amines, secondary amines, and tertiary amines, substituted amines (including naturally occurring substituted amines), cyclamines, basic ion exchange resins, etc. Specific examples of organic bases are isopropylamine, trimethylamine, diethylamine, N-ethylethanamine, tripropylamine and ethanolamine.

The term "stereoisomer" refers to an isomer formed due to the existence of at least one asymmetric center. A compound with one or more asymmetric centers can form a racemate, a racemic mixture, a single enantiomer, a diastereomeric mixture and a single diastereomer. Specific individual molecules may be present as geometric isomers (cis-/trans-). Unless otherwise specified, when a name or structure of a compound having one or more asymmetric centers is disclosed without specifically indicating the stereochemistry, it should be understood that all the possible stereoisomers of the compounds are contemplated.

The term "solvate" refers to a solvate formed by one or more solvent molecules and any of the antibody-drug conjugate of Formula (I) or a pharmaceutically acceptable salt or isomer thereof. The term "solvate" includes a hydrate (e.g., a hemihydrate, monohydrate, dihydrate, trihydrate, tetrahydrate and similar hydrates).

The term "metabolite" refers to a substance generated via oxidation, reduction, hydrolysis, amidation, deamidation, esterification and/or enzymolysis in vivo upon administration.

The term "treatment" or "therapy" as used herein encompasses a maintenance therapy. The term "maintenance therapy" refers to a continued therapy with an effective single-agent chemotherapy after a patient completes a fixed number of chemotherapy cycles in an initial chemotherapy and gets the maximum tumor relief efficacy. In general, the maintenance dose of an agent for a maintenance therapy is relatively low, and thus the adverse reaction is relatively gentle.

The term "insensitive or irresponsive to a treatment with a HER2-targeting agent" as used herein means that a cancer is not effectively controlled and disease progression or relapse occurs, or an expected lesion reduction is not achieved (for example, the decrease of sum of the lesion diameters compared to the sum of the baselines is less than 30%), during a treatment with a HER2-targeting agent or after the last treatment with the same; or it can be determined by a known evaluation method before treatment that the cancer is of a type insensitive or irresponsive to a treatment with a HER2-targeting agent. The cause and mechanism of the insensitivity or irresponsiveness to the treatment may be any one or ones that occur in clinical or preclinical trials, including the drug resistance, e.g., intrinsic drug resistance or acquired drug resistance, of cancer cells to the HER2-targeting agent, or the fact that the cancer is of a low HER2 expression type, or the like. The known evaluation method can include, for example, a method for determining the drug resistance of cancer cells or an immunohistochemistry (IHC) and/or fluorescence in situ hybridization (FISH) test.

The term "drug resistance" as used herein includes "intrinsic drug resistance" and "acquired drug resistance". The former means that cancer cells are insensitive to an agent at the beginning of a treatment, and the latter means that cancer cells initially sensitive to an agent become insensitive after repeated exposure to the agent during the treatment. As an example, cells can be considered as having intrinsic drug resistance in the following situations: disease progression is found in the first imaging evaluation within 3 months or 8-12 weeks after the selection of Trastuzumab as the first-line treatment for metastatic breast cancer; or an event of relapse such as the appearance of a new tumor lesion is diagnosed within 12 months after the selection of Trastuzumab as an adjunct treatment for metastatic breast cancer. As an example, cells can be considered as having acquired drug resistance in the following situations: after an treatment with a regimen involving Trastuzumab, the first imaging evaluation indicates that the disease is remitted or steady, but the disease progresses after a second-line or higher-line treatment, e.g., the diameters of tumor lesions increase (for example, a diameter increases by more than 20%); or an event of relapse such as the appearance of a new tumor lesion is diagnosed within 12 months after the use of Trastuzumab as an adjuvant treatment.

The methods as used herein for determining the HER2 expression level in a patient and the relevant technologies are known in the art. For example, a test for HER2 includes, but is not limited to, a test for HER2 protein by IHC and a test for HER2 gene by FISH technology.

The term "low HER2 expression" as used herein generally refers to a HER2 expression level of IHC 1+, or IHC 2+/FISH negative (i.e., IHC 2+ while FISH test negative), in a clinical test. The terms "high HER2 expression", "HER2 overexpression" and "HER2 positive" are used interchangeably, and generally refer to a HER2 expression level of IHC 2+/FISH positive (i.e., IHC 2+ while FISH test positive), or IHC 3+, in a clinical test. When an IHC staining intensity is reported to be a range, the term "low HER2 expression" as used herein includes the range of IHC 0 to 1+ and IHC 1+ to 2+, in addition to IHC 1+ or IHC 2+/FISH negative. The terms "high HER2 expression", "HER2 overexpression" and "HER2 positive" each include the range of IHC 2+ to 3+, in addition to IHC 2+/FISH positive or IHC 3+. FISH negative as used herein means that a FISH test result shows no amplification of HER2 gene, and FISH positive as used herein means that a FISH test result shows amplification of HER2 gene.

The term "progression of disease" or "disease progression" as used herein means that taking the minimum value of the sum of the diameters of all target lesions in an entire study (if the sum of baselines is the minimum value in the study, this includes the sum of baselines) as reference, the sum of the diameters of the target lesions increases by at least 20%, and the sum of the diameters has an absolute increase of at least 5 mm; or it refers to the appearance of one or more new lesions.

Therapeutic Use and Therapeutic Method

In some embodiments, the present invention provides use of a conjugate of Formula (I), a pharmaceutically acceptable salt, stereoisomer or metabolite thereof, or a solvate of the foregoing in the manufacture of a medicament for the prophylaxis and/or treatment of a cancer insensitive or irresponsive to a treatment with a HER2-targeting agent, Formula (I)

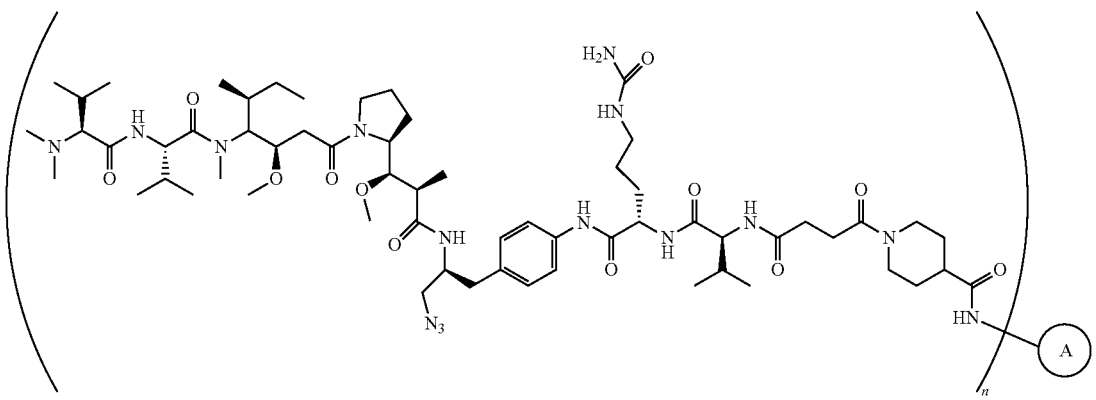

wherein

A is a moiety obtained after the removal of n amino groups from an anti-HER2 antibody or an active fragment or variant thereof, preferably, A is a moiety obtained after the removal of n amino groups from Trastuzumab or Pertuzumab, and n is an integer of 1, 2, 3, 4, 5, 6, 7, or 8.

In some embodiments, the present invention provides a conjugate of Formula (I), a pharmaceutically acceptable salt, stereoisomer or metabolite thereof, or a solvate of the foregoing, as described above, for use in the prophylaxis and/or treatment of a cancer insensitive or irresponsive to a treatment with a HER2-targeting agent.

In some embodiments, the present invention provides a method of preventing and/or treating a cancer insensitive or irresponsive to a treatment with a HER2-targeting agent, comprising administering a therapeutically effective amount of a conjugate of Formula (I), a pharmaceutically acceptable salt, stereoisomer or metabolite thereof, or a solvate of the foregoing, as described above, to a subject in need thereof.

In preferred embodiments, the conjugate of Formula (I) has the structure of Formula (I-1), In preferred embodiments, the cancer insensitive or irresponsive to a treatment with a HER2-targeting agent includes, but is not limited to, a HER2-positive cancer insensitive or irresponsive to a treatment with a HER2-targeting agent.

In preferred embodiments, the HER2-positive cancer insensitive or irresponsive to a treatment with a HER2-targeting agent comprises a HER2-positive cancer with drug resistance (such as intrinsic drug resistance or acquired drug resistance) to a HER2-targeting agent. Preferably, the cancer comprises breast cancer (such as metastatic breast cancer, locally advanced breast cancer or recurrent breast cancer) or gastric cancer (such as advanced gastric cancer or metastatic gastric cancer), or the like.

In preferred embodiments, the cancer insensitive or irresponsive to a treatment with a HER2-targeting agent includes, but is not limited to, a cancer with low HER2 expression. Preferably, the cancer comprises breast cancer (such as metastatic breast cancer, locally advanced breast cancer or recurrent breast cancer) or gastric cancer (such as Formula (I-1)

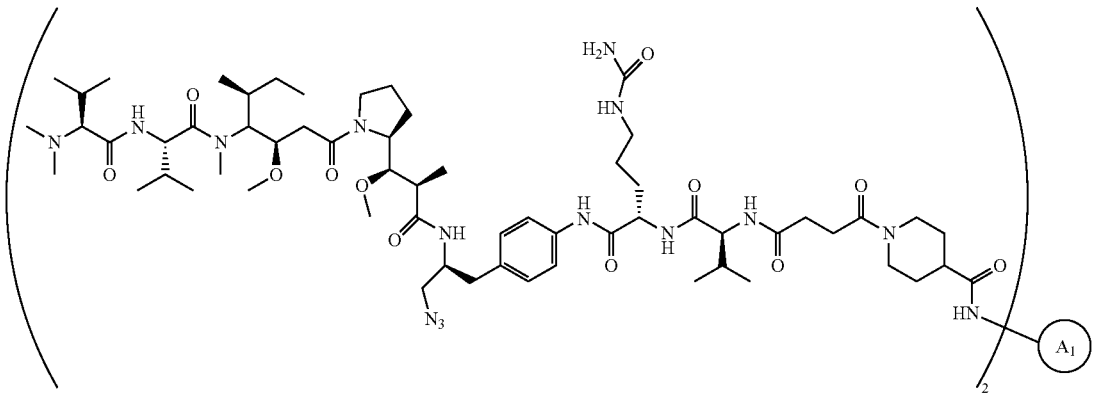

wherein A1 is a moiety obtained after the removal of 2 amino groups from Trastuzumab.

advanced gastric cancer or metastatic gastric cancer) with low HER2 expression, or the like. More preferably, the cancer with low HER2 expression is a cancer with a HER2 expression level of IHC 0 to 1+, IHC 1+, IHC 1+ to 2+ in a clinical test, or an IHC 2+/FISH negative cancer. More preferably, the cancer with low HER2 expression is a cancer with a HER2 expression level of IHC 1+, or an IHC 2+/FISH negative cancer.

In preferred embodiments, the HER2-targeting agent includes: an anti-HER2 antibody drug (such as a monoclonal antibody, an antibody drug conjugate (ADC) or a bispecific antibody), or a chemical drug targeting HER2 (such as lapatinib, neratinib, afatinib or varlitinib). Preferably, the HER2-targeting agent includes Trastuzumab or Pertuzumab or a biosimilar thereof (such as ABP 980, GB221, MYL-14010, CT-P6, EG12014, HD201, ONS-1050, PF-05280014, HD201, Ontruzant or HLX02), or includes an antibody-drug conjugate comprising Trastuzumab or Pertuzumab or a biosimilar thereof as the targeting component (such as an antibody-cytotoxic drug conjugate from conjugation of a targeting component to DM1, DM4, MMAE or MMAF, e.g. T-DM1).

In preferred embodiments, the cancer insensitive or irresponsive to a treatment with a HER2-targeting agent is breast cancer insensitive or irresponsive to a treatment with Trastuzumab and/or T-DM1, preferably HER2 positive breast cancer insensitive or irresponsive to a treatment with Trastuzumab and/or T-DM1.

In preferred embodiments, the cancer insensitive or irresponsive to a treatment with a HER2-targeting agent is breast cancer with drug resistance (such as intrinsic drug resistance or acquired drug resistance) to Trastuzumab and/or T-DM1, preferably HER2 positive breast cancer with drug resistance (such as intrinsic drug resistance or acquired drug resistance) to Trastuzumab and/or T-DM1.

In preferred embodiments, the cancer insensitive or irresponsive to a treatment with a HER2-targeting agent is breast cancer with low HER2 expression, preferably breast cancer with low HER2 expression insensitive or irresponsive to a treatment with Trastuzumab and/or T-DM1.

In preferred embodiments, the phrase "a treatment with a HER2-targeting agent" in the phrase "a cancer insensitive or irresponsive to a treatment with a HER2-targeting agent" as used herein comprises a treatment with Trastuzumab and/or a treatment with T-DM1. Preferably, the treatment is selected from the group consisting of:
 (1) a treatment of breast cancer with Trastuzumab, comprising a first loading dose of intravenous infusion at 4 mg/kg body weight, and then a maintenance dose of weekly intravenous infusion at 2 mg/kg body weight, with the treatment maintained until disease progression; alternatively, comprising a first loading dose of intravenous infusion at 8 mg/kg body weight, and then a maintenance dose of intravenous infusion every 3 weeks at 6 mg/kg body weight, with the treatment maintained until disease progression;
 (2) an adjuvant treatment of breast cancer with Trastuzumab, comprising a first loading dose of intravenous infusion at 8 mg/kg body weight, and then a maintenance dose of intravenous infusion every 3 weeks at 6 mg/kg body weight, in a course of treatment of 52 weeks; alternatively, comprising a first loading dose of intravenous infusion at 4 mg/kg body weight, and then a maintenance dose of weekly intravenous infusion at 2 mg/kg body weight for 12 weeks (combined with paclitaxel or docetaxel) or 18 weeks (combined with docetaxel/carboplatin), followed by a maintenance dose of intravenous infusion every 3 weeks at 6 mg/kg body weight, in a course of treatment of 52 weeks;
 (3) a treatment of gastric cancer with Trastuzumab, comprising a first loading dose of intravenous infusion at 8 mg/kg body weight, and then a maintenance dose of intravenous infusion every 3 weeks at 6 mg/kg body weight, with the treatment maintained until disease progression; or
 (4) a treatment of breast cancer with T-DM1, comprising intravenous infusion every 3 weeks at 3.6 mg/kg body weight, with the treatment maintained until disease progression or unacceptable toxicity.

In preferred embodiments, the prophylaxis and/or treatment comprises administering to a patient a therapeutically effective amount of a conjugate of Formula (I) (preferably a conjugate of Formula (I-1)), a pharmaceutically acceptable salt, stereoisomer or metabolite thereof, or a solvate of the foregoing, preferably at a dose of 0.1-15 mg/kg body weight, more preferably at a dose of 0.5-10 mg/kg body weight, and most preferably at a dose of 1-8 mg/kg body weight.

In preferred embodiments, the prophylaxis and/or treatment further comprises the step of evaluating whether the patient's cancer is insensitive or irresponsive to a treatment with a HER2-targeting agent prior to the administration. Preferably, the evaluation comprises evaluating whether the patient's cancer has drug resistance (e.g., intrinsic drug resistance and/or acquired drug resistance) to a HER2-targeting agent, or evaluating whether the patient's cancer is a cancer with low HER2 expression. The evaluation can be conducted by a method known in the art.

In preferred embodiments, the prophylaxis and/or treatment comprises the following steps:
 (1) treating a patient having HER2-positive cancer with a HER2-targeting agent and monitoring whether the patient has drug resistance to the HER2-targeting agent; and
 (2) administering a therapeutically effective amount of a conjugate of Formula (I), a pharmaceutically acceptable salt, stereoisomer or metabolite thereof, or a solvate of the foregoing to the patient having HER2-positive cancer with drug resistance to the HER2-targeting agent.

Preferably, the drug resistance is monitored by a tumor imaging test (such as X-ray, CT scan or MRI), or by a detection of a tumor biomarker.

Preferably, the HER2-targeting agent comprises Trastuzumab or T-DM1.

Preferably, the HER2-positive cancer comprises breast cancer (such as metastatic breast cancer, locally advanced breast cancer or recurrent breast cancer) or gastric cancer (such as advanced gastric cancer or metastatic gastric cancer), or the like.

Preferably, the conjugate of Formula (I) is a conjugate of Formula (I-1).

In preferred embodiments, the prophylaxis and/or treatment comprises the following steps:
 (1) treating a patient having HER2-positive cancer with a HER2-targeting agent and monitoring the disease progression of the cancer; and
 (2) administering a therapeutically effective amount of a conjugate of Formula (I), a pharmaceutically acceptable salt, stereoisomer or metabolite thereof, or a solvate of the foregoing to the patient upon disease progression.

Preferably, the disease progression of the cancer is monitored by a tumor imaging test (such as X-ray, CT scan or MRI), or by a detection of a tumor biomarker.

Preferably, the monitoring of the disease progression of the cancer comprises comparing the tumor at a second time point with the tumor at a first time point, wherein the first time point is before or after the treatment with a HER2-targeting agent, and the second time point is after the first time point.

Preferably, the HER2-targeting agent comprises Trastuzumab or T-DM1.

Preferably, the HER2-positive cancer comprises breast cancer (such as metastatic breast cancer, locally advanced breast cancer or recurrent breast cancer) or gastric cancer (such as advanced gastric cancer or metastatic gastric cancer), or the like.

Preferably, the conjugate of Formula (I) is a conjugate of Formula (I-1).

In preferred embodiments, the prophylaxis and/or treatment comprises the following steps:
(1) testing the HER2 expression level in a cancer patient; and
(2) when the HER2 expression is low, administering a therapeutically effective amount of a conjugate of Formula (I), a pharmaceutically acceptable salt, stereoisomer or metabolite thereof, or a solvate of the foregoing to the patient.

Preferably, the HER2-targeting agent comprises Trastuzumab or T-DM1.

Preferably, the cancer comprises breast cancer (such as metastatic breast cancer, locally advanced breast cancer or recurrent breast cancer) or gastric cancer (such as advanced gastric cancer or metastatic gastric cancer), or the like.

Preferably, the conjugate of Formula (I) is a conjugate of Formula (I-1).

EXAMPLES

The present invention will be further illustrated by the following examples. These examples are used to illustrate the present invention only, but not limit the present invention in any way.

In Examples 1 and 2, the anti-tumor effect of the conjugate of Formula (I-1) on tumor-bearing mice subcutaneously transplanted with human tumor cells or human-derived tumor tissues was evaluated. In particular, the conjugate of Formula (I-1) was administered by a single dose injection through tail vein to transplanted tumor model mice transplanted subcutaneously with human breast cancer cell line JIMT-1 (HER2-positive breast cancer cell line, Trastuzumab resistant cell strain, M Barok et al., Breast Cancer Res., Apr. 21, 2011, 13 (2): R46; Marvi Jumppanen, Basal Cytokeratins and HER-2 Oncogene in Breast Cancer, 2007), and PDX humanized breast cancer xenograft mice animal model BR0438 (low HER2 expression, IHC 1+ to 2+). The changes of tumor volume and animal body weight were measured twice a week, and efficacy (anti-tumor efficacy) of the conjugate of Formula (I-1) on the tumor-bearing mice was calculated.

Test Agent

Appropriate amounts of Trastuzumab (naked antibody, Sichuan Kelun Pharmaceutical Research Institute Co., Ltd.), T-DM1 (KADCYLA®, Roche Pharmaceuticals) and the antibody-drug conjugate of Formula (I-1) (Sichuan Kelun Pharmaceutical Research Institute Co., Ltd.) were separately taken to prepare mother liquors of certain concentrations with sterile ultra-pure water. After gently shaking, those were dispensed and stored at −20° C. They were diluted with normal saline based on dose to obtain solutions of the treatment groups for use. At the same time, a blank control group was set (the blank control group differs from the antibody-drug conjugate of Formula (I-1) group by not containing an API).

Test Animals and Cell Lines

NOD/SCID mice (Beijing HFK Bio-Technology Co., Ltd.).

Breast cancer cell line JIMT-1 (AddexBio), PDX humanized breast cancer tumor xenograft mice animal model BR0438 (Crown Bioscience International).

Experimental Grouping and Evaluation Method

The tumor-bearing mice with tumor volume of 100-200 mm$^3$ were randomly assigned (the number of samples in each group was determined according to sample quantity), 8 mice per group. The dosing volume was 10 mL/kg body weight. The route of administration was a single dose injection through tail vein. After administration, the tumor diameter was measured with vernier caliper twice a week for an observation period of 4 weeks, and the tumor volume was calculated according to the following equation: V=0.5 a×b$^2$, wherein a and b represent the major diameter and the minor diameter of the tumor, respectively. Animal deaths were observed and recorded daily.

The tumor growth inhibition TGI (%) was calculated with the following equation for evaluating the anti-tumor efficacy of the antibody-drug conjugate:

$$TGI\ (\%) = [1-(V_{Te}-V_{Ts})/(V_{Ce}-V_{Cs})]*100\%$$

wherein $V_{Te}$: Average tumor volume of treatment group at the end of test $V_{Ts}$: Average tumor volume of treatment group at the start of administration $V_{Ce}$: Average tumor volume of blank control group at the end of test $V_{Cs}$: Average tumor volume of blank control group at the start of administration Example 1. Human Breast Cancer JIMT-1 Model Test Method:

JIMT-1 cells were cultured in DMEM medium containing 10% fetal bovine serum at 37° C. and 5% $CO_2$. JIMT-1 cells in exponential growth phase were collected, resuspended in PBS to a suitable concentration, and subcutaneously inoculated into female NOD/SCID mice to establish a breast cancer model. When the tumors grew to an average volume of about 122 mm$^3$, mice were randomly grouped according to tumor volumes. After grouping, blank control, T-DM1, Trastuzumab naked antibody, and low, medium, and high doses of the antibody-drug conjugate of Formula (I-1) were separately administered by a single dose injection through tail vein. The tumor volumes and the body weights of the mice were observed and regularly measured after the injection. The specific results are shown in Table 1-1, Table 1-2 and FIGS. 1-2.

Test Results:

The human breast cancer cell line JIMT-1 used in this example was a HER2-positive Trastuzumab-resistant cell line (M. Barok et al., Breast Cancer Res., Apr. 21, 2011; 13(2): R46.). A human breast cancer subcutaneous transplantation tumor model was constructed with this cell line to evaluate and compare the antitumor efficacy of the antibody-drug conjugate of Formula (I-1), Trastuzumab naked antibody and T-DM1.

TABLE 1-1

Human breast cancer JIMT-1 model

| Grouping | Group | Day 43 Tumor Volume (mm³) (Average ± S) | TGI (%) | P value* (vs. Group 1) |
|---|---|---|---|---|
| Group 1 | Blank control | 1428 ± 116 | — | — |
| Group 2 | T-DM1 10 mg/kg | 1059 ± 97 | 28 | 0.029 |
| Group 3 | Trastuzumab naked antibody 10 mg/kg | 1233 ± 106 | 15 | 0.238 |
| Group 4 | the antibody-drug conjugate of Formula (I-1) 1 mg/kg | 778 ± 101 | 50 | <0.001 |
| Group 5 | the antibody-drug conjugate of Formula (I-1) 3 mg/kg | 215 ± 45 | 93 | <0.001 |
| Group 6 | the antibody-drug conjugate of Formula (I-1) 10 mg/kg | 7 ± 3 | 109 | <0.001 |

*P value less than 0.05 indicates a significant difference.

It can be concluded from Table 1-1 that the Trastuzumab naked antibody group did not have a significant difference in tumor growth inhibition compared to the blank control group, indicating that the Trastuzumab naked antibody exerted no inhibitory effect on the tumor growth of model mice with JIMT-1 breast cancer xenograft resistant to Trastuzumab; T-DM1 displayed a weak inhibitory effect on tumor growth, while low, medium, and high doses of the antibody-drug conjugate of Formula (I-1) all significantly and dose-dependently inhibited the tumor growth.

The comparison of therapeutic effect between the antibody-drug conjugate of Formula (I-1) and T-DM1 is shown in Table 1-2.

TABLE 1-2

Human breast cancer JIMT-1 model

| Grouping | Group | Day 43 Tumor Volume (mm³) (Average ± S) | TGI (%) | P value* (vs. Group 2) |
|---|---|---|---|---|
| Group 1 | Blank control | 1428 ± 116 | — | — |
| Group 2 | T-DM1 10 mg/kg | 1059 ± 97 | 28 | — |
| Group 4 | the antibody-drug conjugate of Formula (I-1) 1 mg/kg | 778 ± 101 | 50 | 0.064 |
| Group 5 | the antibody-drug conjugate of Formula (I-1) 3 mg/kg | 215 ± 45 | 93 | <0.001 |
| Group 6 | the antibody-drug conjugate of Formula (I-1) 10 mg/kg | 7 ± 3 | 109 | <0.001 |

*P value less than 0.05 indicates a significant difference.

It can be concluded from Table 1-2 that compared to T-DM1, the anti-tumor efficacy of both medium and high doses of the antibody-drug conjugate of Formula (I-1) was significantly better than T-DM1 (P<0.001); the low-dose group and T-DM1 showed no statistically significant difference in tumor growth inhibition (P>0.05), though the two indicators of inhibition rates of tumor growth and tumor volume were both significantly better than T-DM1 again.

Figure 2:
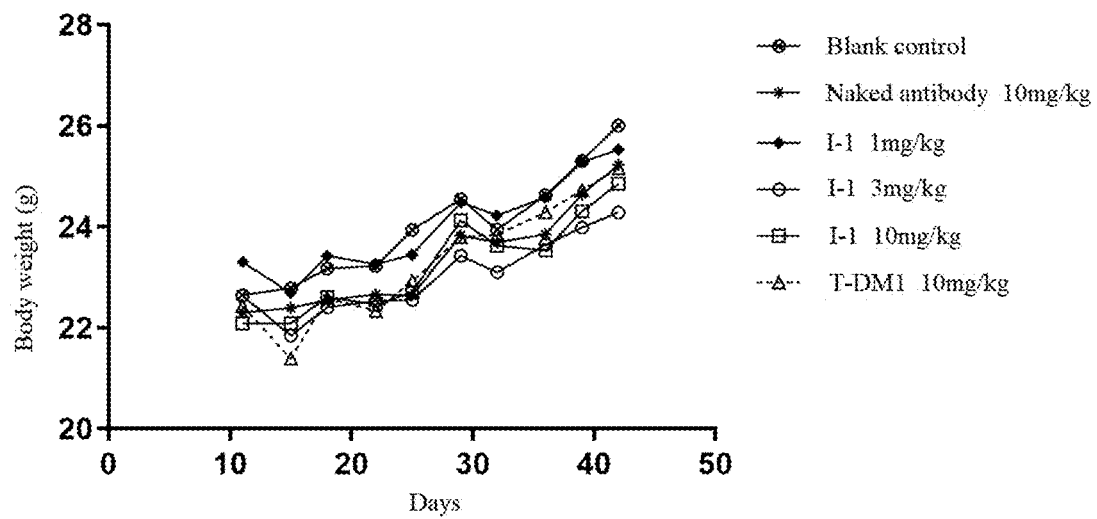
FIG. 2 shows the changes in body weight of the mice in each group in a human breast cancer JIMT-1 model.

It can be concluded from FIG. 2 that all the treatment groups shown in Tables 1-1 and 1-2 had no animal death or significant animal weight loss during the observation period, and no obvious drug toxicity was observed. During the treatment period, the mice tolerated well with each of the test agents.

Example 2. Breast Cancer Tumor Xenograft Model BR0438

Figure 3:
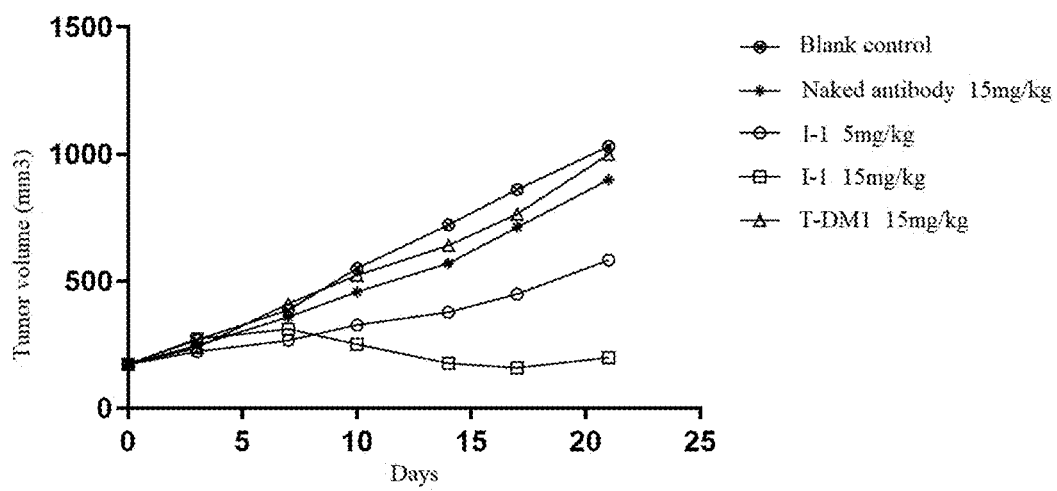
FIG. 3 shows the changes in tumor growth by volume of the BR0438 tumor-bearing mice in a breast cancer xenograft model after administration.
Figure 4:
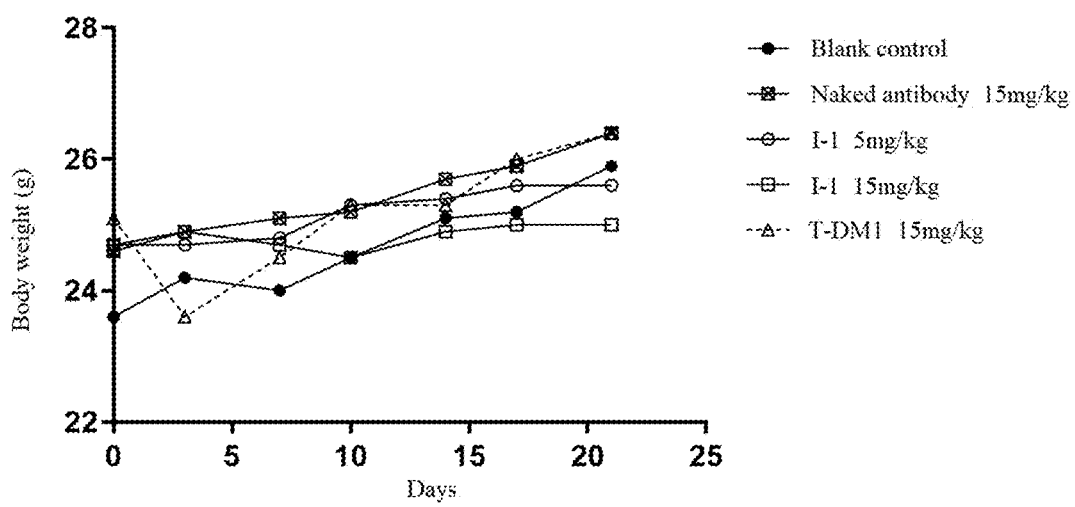
FIG. 4 shows the changes in body weight of the BR0438 tumor-bearing mice in a breast cancer xenograft model after administration.

Test Method:

BR0438 is a xenograft model established from a breast cancer tumor derived from a 53-year-old female patient. The patient was pathologically diagnosed with breast invasive ductal carcinoma and displayed low HER2 expression (IHC 1+ to 2+). NOD/SCID mice were subcutaneously inoculated with BR0438 tumor to establish a human breast cancer subcutaneous transplantation tumor model. When the tumors grew to an average volume of about 173 mm³, mice were randomly grouped according to tumor volumes. After grouping, blank control, T-DM1, Trastuzumab naked antibody, and low, medium, and high doses of the antibody-drug conjugate of Formula (I-1) were separately administered by a single dose injection through tail vein. The tumor volumes and the body weights of the mice were regularly observed and measured after the injection. The specific results are shown in Table 2 and FIGS. 3-4.

TABLE 2

PDX breast cancer tumor xenograft model BR0438

| Grouping | Group | Day 21 Tumor Volume (mm³) (Average ± S) | TGI (%) | P value* (vs. Group 1) | P value* (vs. Group 2) |
|---|---|---|---|---|---|
| Group 1 | Blank control | 1030 ± 110 | — | — | — |
| Group 2 | T-DM1 15 mg/kg | 999 ± 108 | 3.65% | 1 | — |
| Group 3 | Trastuzumab naked antibody 15 mg/kg | 899 ± 94 | 15.31% | 0.776 | — |
| Group 4 | the antibody-drug conjugate of Formula (I-1) 5 mg/kg | 583 ± 58 | 52.18% | 0.002 | 0.004 |

TABLE 2-continued

PDX breast cancer tumor xenograft model BR0438

| | | Day 21 | | | |
|---|---|---|---|---|---|
| Grouping | Group | Tumor Volume (mm$^3$) (Average ± S) | TGI (%) | P value* (vs. Group 1) | P value* (vs. Group 2) |
| Group 5 | the antibody-drug conjugate of Formula (I-1) 15 mg/kg | 199 ± 56 | 96.99% | <0.001 | <0.001 |

*P value less than 0.05 indicates a significant difference.

Test Results:

It can be concluded from Table 2 that compared to the blank control group, neither the Trastuzumab naked antibody group nor the T-DM1 group displayed a significant difference in tumor growth inhibition, indicating that the Trastuzumab naked antibody and T-DM1 exerted no inhibitory effect on the tumor growth of BR0438 breast cancer xenograft model mice, while the low and high doses of the antibody-drug conjugate of Formula (I-1) both significantly and dose-dependently inhibited the tumor growth. Also, it can be concluded from FIG. 4 that there was no animal death or significant weight loss in all treatment groups during the observation period, and no obvious drug toxicity was observed. During the treatment period, the mice tolerated well with each of the test agents.

For breast cancer tumors with low HER2 expression, Trastuzumab and T-DM1 did not show a therapeutic effect, while the antibody-drug conjugate of Formula (I-1) of the present invention had a significant inhibitory effect and is expected to be used for patients having tumors with low HER2 expression and irresponsive to therapies with Trastuzumab and T-DM1.

In summary, the antibody-drug conjugate of Formula (I) of the present invention is expected to treat patients having breast cancer insensitive or irresponsive to a treatment with a HER2-targeting agent such as Trastuzumab and/or T-DM1, e.g., patients having breast cancer with drug resistance or low HER2 expression, and is expected to bring clinical benefits to more patients.

Although the present invention has been illustrated by way of the specific examples above, it should not be interpreted as being limited to the examples. The present invention contemplates the general aspects disclosed above, and those skilled in the art can make various modifications or changes to the various details of the present invention without departing from the spirit and scope of the present invention. Therefore, the specification is for illustrative purpose only, not for any restrictions.

What is claimed is:

1. A method of treating a cancer insensitive or irresponsive to a treatment with a HER2-targeting agent, comprising administering a therapeutically effective amount of a conjugate of Formula (I), a pharmaceutically acceptable salt or stereoisomer thereof, or a solvate of the foregoing to a subject in need thereof,

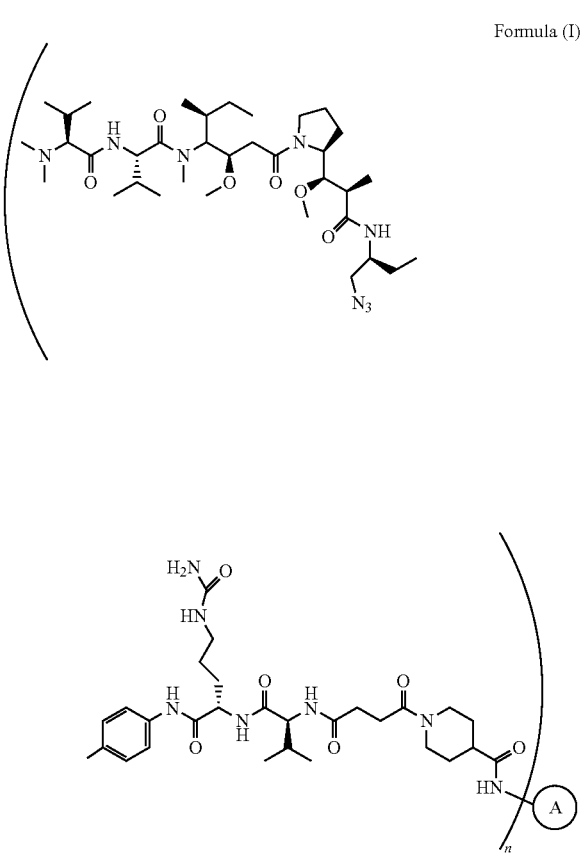

Formula (I)

wherein
A is a moiety obtained after the removal of n amino groups from an anti-HER2 antibody or an active fragment thereof, and n is an integer of 1, 2, 3, 4, 5, 6, 7, or 8.

2. The method according to claim 1, wherein the conjugate of Formula (I) has the structure represented by Formula (I-1), Formula (I-1)

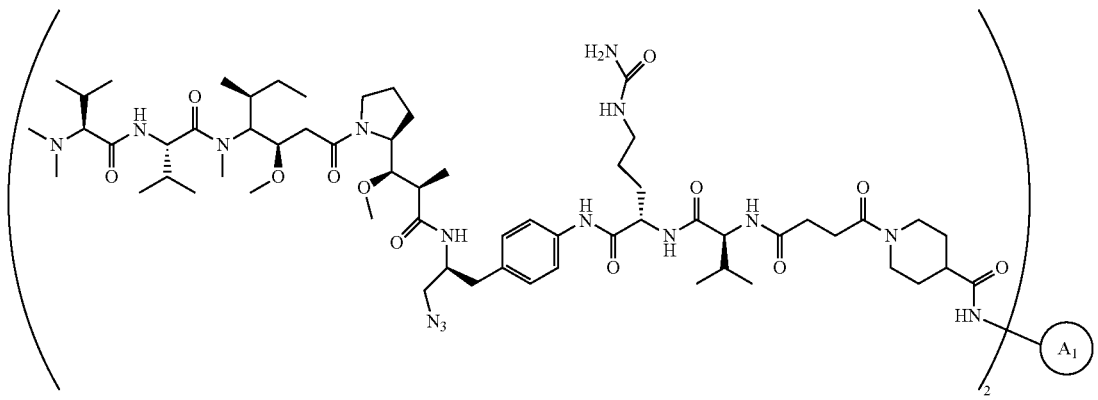

wherein $A_1$ is a moiety obtained after the removal of 2 amino groups from Trastuzumab.

3. The method according to claim 1, wherein the cancer is a breast or gastric cancer, and the breast or gastric cancer comprises a HER2-positive breast or gastric cancer insensitive or irresponsive to a treatment with a HER2-targeting agent.

4. The method according to claim 3, wherein the HER2-positive breast or gastric cancer comprises a HER2-positive breast or gastric cancer with drug resistance to a HER2-targeting agent.

5. The method according to claim 1, wherein the cancer comprises a breast or gastric cancer with low HER2 expression.

6. The method according to claim 5, wherein the breast or gastric cancer with low HER2 expression is a breast or gastric cancer with a HER2 expression level of IHC 1+, IHC 1+ to 2+ in a clinical test, or an IHC 2+/FISH negative breast or gastric cancer.

7. The method according to claim 1, wherein the HER2-targeting agent is selected from the group consisting of an anti-HER2 monoclonal antibody, an anti-HER2 antibody drug conjugate (ADC), an anti-HER2 bispecific antibody and a chemical drug targeting HER2.

8. The method according to claim 1, wherein the treatment with a HER2-targeting agent comprises a treatment with Trastuzumab and/or T-DM1.

9. The method according to claim 1, wherein the method comprises administering to a patient a therapeutically effective amount of the conjugate of Formula (I), the pharmaceutically acceptable salt or stereoisomer thereof or the solvate of the foregoing at a dose of 0.1-15 mg/kg body weight.

10. The method according to claim 9, wherein the method further comprises the step of evaluating whether the patient's cancer is insensitive or irresponsive to a treatment with a HER2-targeting agent prior to the administration, wherein the patient's cancer is a breast or gastric cancer, and the evaluation comprises evaluating whether the patient's breast or gastric cancer has drug resistance to a HER2-targeting agent, or evaluating whether the patient's breast or gastric cancer is a cancer with low HER2 expression.

11. The method according to claim 1, wherein the method comprises the following steps:
  (1) treating a patient having HER2-positive cancer with a HER2-targeting agent and monitoring whether the patient has drug resistance to the HER2-targeting agent, wherein the patient's cancer is a breast or gastric cancer; and
  (2) administering a therapeutically effective amount of the conjugate of Formula (I), the pharmaceutically acceptable salt or stereoisomer thereof, or the solvate of the foregoing to the patient having HER2-positive breast or gastric cancer with drug resistance to the HER2-targeting agent.

12. The method according to claim 1, wherein the method comprises the following steps:
  (1) treating a patient having HER2-positive cancer with a HER2-targeting agent and monitoring the disease progression of the cancer, wherein the HER2-positive cancer is a breast or gastric cancer; and
  (2) administering a therapeutically effective amount of the conjugate of Formula (I), the pharmaceutically acceptable salt or stereoisomer thereof, or the solvate of the foregoing to the patient upon disease progression.

13. The method according to claim 1, wherein the method comprises the following steps:
  (1) testing the HER2 expression level in a cancer patient, wherein the cancer is a breast or gastric cancer; and
  (2) when the HER2 expression is low, administering a therapeutically effective amount of the conjugate of Formula (I), the pharmaceutically acceptable salt or stereoisomer thereof, or the solvate of the foregoing to the patient.

14. The method according to claim 2, wherein the cancer comprises a HER2-positive breast or gastric cancer insensitive or irresponsive to a treatment with a HER2-targeting agent.

15. The method according to claim 2, wherein the cancer comprises a breast or gastric cancer with low HER2 expression.

16. The method according to claim 2, wherein the HER2-targeting agent is Trastuzumab, Pertuzumab, ABP 980, GB221, MYL-1401O, CT-P6, EG12014, HD201, ONS-1050, PF-05280014, HD201, Trastuzumab-dttb or HLX02, or an antibody-drug conjugate comprising Trastuzumab, Pertuzumab, ABP 980, GB221, MYL-1401O, CT-P6, EG12014, HD201, ONS-1050, PF-05280014, HD201, Trastuzumab-dttb or HLX02.

17. The method according to claim 2, wherein the method comprises administering to a cancer patient a therapeutically effective amount of the conjugate of Formula (I-1), the pharmaceutically acceptable salt or stereoisomer thereof or the solvate of the foregoing at a dose of 0.1-15 mg/kg body weight, wherein the cancer is a breast or gastric cancer.

18. The method according to claim 17, wherein the method further comprises the step of evaluating whether the patient's breast or gastric cancer is insensitive or irresponsive to a treatment with a HER2-targeting agent prior to the administration.

19. The method according to claim 1, wherein, A is a moiety obtained after the removal of n amino groups from Trastuzumab or Pertuzumab.

20. The method according to claim 4, wherein the breast cancer is metastatic breast cancer, locally advanced breast cancer or recurrent breast cancer; and the gastric cancer is advanced gastric cancer or metastatic gastric cancer.

21. The method according to claim 5, wherein the breast cancer is metastatic breast cancer, locally advanced breast cancer or recurrent breast cancer; and the gastric cancer is advanced gastric cancer or metastatic gastric cancer.

22. The method according to claim 7, wherein the HER2-targeting agent is Trastuzumab, Pertuzumab, ABP 980, GB221, MYL-1401O, CT-P6, EG12014, HD201, ONS-1050, PF-05280014, HD201, Trastuzumab-dttb or HLX02, or an antibody-drug conjugate comprising Trastuzumab, Pertuzumab, ABP 980, GB221, MYL-1401O, CT-P6, EG12014, HD201, ONS-1050, PF-05280014, HD201, Trastuzumab-dttb or HLX02 as the targeting component.

23. The method according to claim 14, wherein the HER2-positive breast or gastric cancer comprises a HER2-positive breast or gastric cancer with drug resistance to a HER2-targeting agent.

24. The method according to claim 23, wherein the breast cancer is metastatic breast cancer, locally advanced breast cancer or recurrent breast cancer; and the gastric cancer is advanced gastric cancer or metastatic gastric cancer.

25. The method according to claim 15, wherein the breast cancer is metastatic breast cancer, locally advanced breast cancer or recurrent breast cancer; and the gastric cancer is advanced gastric cancer or metastatic gastric cancer.

26. The method according to claim 25, wherein the breast or gastric cancer with low HER2 expression is a breast or gastric cancer with a HER2 expression level of IHC 1+, IHC 1+ to 2+ in a clinical test, or an IHC 2+/FISH negative breast or gastric cancer.

* * * * *